US009513380B2

(12) United States Patent
Liu

(10) Patent No.: US 9,513,380 B2
(45) Date of Patent: Dec. 6, 2016

(54) X-RAY DETECTORS SUPPORTED ON A SUBSTRATE HAVING A SURROUNDING METAL BARRIER

(71) Applicant: GENERAL ELECTRIC COMPANY, Schenectady, NY (US)

(72) Inventor: Jie Jerry Liu, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 111 days.

(21) Appl. No.: 14/340,948

(22) Filed: Jul. 25, 2014

(65) Prior Publication Data

US 2016/0027847 A1 Jan. 28, 2016

(51) Int. Cl.

| | |
|---|---|
| ***G01T 1/20*** | (2006.01) |
| ***G01T 1/24*** | (2006.01) |
| ***A61B 6/00*** | (2006.01) |
| ***G01N 23/04*** | (2006.01) |
| ***H01L 27/30*** | (2006.01) |
| ***H01L 51/00*** | (2006.01) |
| ***H01L 51/44*** | (2006.01) |
| ***G01T 1/202*** | (2006.01) |

(52) U.S. Cl.

CPC ............... *G01T 1/2018* (2013.01); *A61B 6/42* (2013.01); *A61B 6/4233* (2013.01); *G01N 23/04* (2013.01); *G01T 1/202* (2013.01); *G01T 1/24* (2013.01); *H01L 27/308* (2013.01); *H01L 51/0021* (2013.01); *H01L 51/0097* (2013.01); *H01L 51/44* (2013.01)

(58) Field of Classification Search

CPC .... A61B 6/42; A61B 6/4233; G01T 1/2018; G01T 1/24

USPC .............................. 378/19, 98.8; 250/370.09

See application file for complete search history.

(56) References Cited

U.S. PATENT DOCUMENTS

| | | | | |
|---|---|---|---|---|
| 6,594,339 | B1 * | 7/2003 | Alving | A61B 6/488 378/98.7 |
| 6,743,524 | B2 | 6/2004 | Schaepkens | |
| 6,856,670 | B2 * | 2/2005 | Hoheisel | H01L 27/14658 250/370.09 |
| 7,034,306 | B2 | 4/2006 | Homme et al. | |
| 7,115,878 | B2 | 10/2006 | Ikeda et al. | |

(Continued)

FOREIGN PATENT DOCUMENTS

JP 01267500 A 10/1989

OTHER PUBLICATIONS

PCT Search Report and Written Opinion issued in connection with corresponding PCT Application No. PCT/US2015/041488 dated Nov. 3, 2015.

(Continued)

*Primary Examiner* — Allen C. Ho

(74) *Attorney, Agent, or Firm* — Heslin Rothenberg Farley & Mesiti P.C.

(57) ABSTRACT

An X-ray detector assembly includes a polymeric substrate having a lower surface and an upper surface, and an X-ray detector disposed on the upper surface of the substrate. The X-ray detector includes a thin-film-transistor array disposed on the substrate, an organic photodiode disposed on the thin-film-transistor array, and a scintillator disposed on the organic photodiode. A metal barrier extends substantially over an upper surface of the scintillator, substantially over peripherally-extending edges of the scintillator, the organic photodiode, and the thin-film-transistor array, and substantially over the lower surface of the substrate.

34 Claims, 6 Drawing Sheets

(56) References Cited

U.S. PATENT DOCUMENTS

| | | | |
|---|---|---|---|
| 7,126,128 B2 | 10/2006 | Ikeda et al. | |
| 7,387,920 B2 | 6/2008 | Cho | |
| 7,402,814 B2 | 7/2008 | Vieux et al. | |
| 7,408,177 B2 | 8/2008 | Homme et al. | |
| 7,449,249 B2 | 11/2008 | Barbezat | |
| 7,514,686 B2 * | 4/2009 | Ogawa | G01T 1/2002 250/361 R |
| 7,541,671 B2 | 6/2009 | Foust et al. | |
| 7,567,649 B1 * | 7/2009 | Safai | G01T 1/24 250/370.09 |
| 7,569,832 B2 * | 8/2009 | Tredwell | G01T 1/2018 250/370.11 |
| 7,705,315 B2 | 4/2010 | Homme et al. | |
| 7,816,676 B2 | 10/2010 | Fourst et al. | |
| 7,956,332 B2 * | 6/2011 | Burr | G01T 1/20 250/361 R |
| 8,102,119 B2 | 1/2012 | Farquhar et al. | |
| 8,173,969 B2 * | 5/2012 | Nishino | G01T 1/2018 250/370.08 |
| 8,236,424 B2 | 8/2012 | Schaepkens et al. | |
| 8,350,470 B2 | 1/2013 | Farquhar et al. | |
| 8,497,481 B2 * | 7/2013 | Shinba | G01T 1/2018 250/366 |
| 8,581,254 B2 | 11/2013 | Couture et al. | |
| 8,605,862 B2 | 12/2013 | Granfors et al. | |
| 9,285,489 B2 * | 3/2016 | Couture | G01T 1/2018 |
| 2006/0033032 A1 | 2/2006 | Inoue et al. | |
| 2012/0219114 A1 | 8/2012 | Iwakiri et al. | |
| 2012/0223240 A1 | 9/2012 | Ichimura et al. | |
| 2013/0037723 A1 | 2/2013 | Verschuren et al. | |
| 2015/0171134 A1 * | 6/2015 | Couture | H01L 27/14632 250/366 |

OTHER PUBLICATIONS

Iacchetti A et al.,"Multi-Layer Organic Squaraine-Based Photodiode for Indirect X-Ray Detection", Nuclear Science, IEEE Transactions on, IEEE, Oct. 2012, pp. 1862-1867, vol. 59, Issue:5.

Gerwin H Gelinck et al., "X-ray imager using solution processed organic transistor arrays and bulk heterojunction photodiodes thin, flexible plastic substrate", Organic Electronics, ScienceDirect, Oct. 2013, pp. 2602-2609, vol. 14, Issue:10.

Gautam Parthasarathy et al., pending design U.S. Appl. No. 13/955,355, entitled "Organic X-Ray Detector", filed Jul. 31, 2013, 22-pages.

Couture et al., pending design U.S. Appl. No. 14/014,003 entitled "Organic X-Ray Detector Assembly and Method of Manufacturing Same", filed Aug. 29, 2013, 41-pages.

Pending design U.S. Appl. No. 14/144,253 entitled "Method of Manufacturing Photodiode Detectors", filed Dec. 30, 2013, 27-pages.

Couture et al., pending design U.S. Appl. No. 14/103,989 entitled "Optoelectronic Device With Flexible Substrate", filed Dec. 12, 2013, 12-pages.

Couture et al., pending design U.S. Appl. No. 14/109,454 entitled "Method and System for Integrated Medical Transport Backboard Digital X-Ray Imaging Detector", filed Dec. 17, 2013, 21-pages.

* cited by examiner

X-RAY DETECTORS SUPPORTED ON A SUBSTRATE HAVING A SURROUNDING METAL BARRIER

TECHNICAL FIELD

The present disclosure relates generally to X-ray detectors, and more particularly, to X-ray detectors supported on a substrate having a surrounding metal barrier.

BACKGROUND

X-ray radiation detectors include an electronically or optically active portion, e.g., radiation detector that is frequently disposed on a substrate. In those applications where a rigid electro-optical device is either preferable or acceptable, either glass or silicon is generally used as the substrate. In those applications where a flexible electro-optical device is desired, a polymeric film may serve as the substrate. However, moisture and oxygen diffuse rapidly through such polymeric film substrates, thereby causing the performance of the electro-optical devices disposed on the substrate to degrade or even fail. In addition, polymeric substrates are also subject to attack by chemicals used during processing of the electro-optical device.

U.S. Pat. No. 8,236,424 issued to Schaepkens et al. discloses an electro-optical device having at least one base and a multilayer coating surface disposed on at least one surface of the base. The at least one base may include either an optically or electronically active portion or a flexible polymeric material. The multilayer coating set includes at least one organic layer and at least one inorganic layer. The base and multilayer coating set are transparent to light in the visible portion of the spectrum. The inorganic layer may include at least one of silicon, a metal oxide, a metal nitride, and combinations thereof, and having a thickness of about 20 nanometers to about 200 nanometers. The multilayer coating set provides a barrier to moisture and oxygen and provides chemical resistance. The multilayer coating set is also mechanically flexible and thermally stable up to a glass transition temperature of the base.

There is a need for further X-ray detectors, and more particularly, to organic X-ray detectors supported on a substrate having a surrounding metal barrier.

SUMMARY

In an aspect of the present disclosure, an X-ray detector assembly includes a polymeric substrate having a lower surface and an upper surface, and an X-ray detector disposed on the upper surface of the substrate. The X-ray detector includes a thin-film-transistor array disposed on the substrate, an organic photodiode disposed on the thin-film-transistor array, and a scintillator disposed on the organic photodiode. A metal barrier extends substantially over an upper surface of the scintillator, substantially over peripherally-extending edges of the scintillator, the organic photodiode, and the thin-film-transistor array, and substantially over the lower surface of the substrate.

In another aspect of the present disclosure, an X-ray system includes the above-noted X-ray detector assembly, an X-ray source, and a controller operable for controlling the X-ray source and the X-ray detector.

In another aspect of the present disclosure, a method for fabricating an X-ray detector assembly includes providing a polymeric substrate having a lower surface and an upper surface, providing an X-ray detector disposed on the upper surface of the substrate, the X-ray detector includes a thin-film-transistor array, an organic photodiode, and a scintillator, and providing a metal barrier providing a barrier to oxygen and moisture extending substantially over an upper surface of the scintillator, substantially over peripherally-extending edges of the scintillator, the organic photodiode, and the thin-film-transistor array, and substantially over the lower surface of the substrate.

DRAWINGS

The foregoing and other features, aspects and advantages of this disclosure will become apparent from the following detailed description of the various aspects of the disclosure taken in conjunction with the accompanying drawings, wherein.

DETAILED DESCRIPTION

As described in greater detail below, the present disclosure is to X-ray detectors employing a surrounding metal barrier layer that may improve X-ray detector reliability. For example, the metal barrier layer may form a seal or barrier to oxygen and moisture for protecting the components of the X-ray detector and the supporting substrate. Such a technique may be desirable for mechanically flexible X-ray detectors having a polymeric or plastic substrate. The metal barrier may be a solid metal coating or a metal foil such as including substantially one or more elemental metals, and substantially not include oxides.

Each embodiment presented below facilitates the explanation of certain aspects of the disclosure, and should not be interpreted as limiting the scope of the disclosure. Moreover, approximating language, as used herein throughout the specification and claims, may be applied to modify any quantitative representation that could permissibly vary without resulting in a change in the basic function to which it is related. Accordingly, a value modified by a term or terms, such as "about," is not limited to the precise value specified. In some instances, the approximating language may correspond to the precision of an instrument for measuring the value. When introducing elements of various embodiments, the articles “a,” “an,” “the,” and “said” are intended to mean that there are one or more of the elements. The terms “comprising,” “including,” and “having” are intended to be inclusive and mean that there may be additional elements other than the listed elements. As used herein, the terms “may” and “may be” indicate a possibility of an occurrence within a set of circumstances; a possession of a specified property, characteristic or function; and/or qualify another verb by expressing one or more of an ability, capability, or possibility associated with the qualified verb. Accordingly, usage of “may” and “may be” indicates that a modified term is apparently appropriate, capable, or suitable for an indicated capacity, function, or usage, while taking into account that in some circumstances, the modified term may sometimes not be appropriate, capable, or suitable. Any examples of operating parameters are not exclusive of other parameters of the disclosed embodiments. Components, aspects, features, configurations, arrangements, uses and the like described, illustrated or otherwise disclosed herein with respect to any particular embodiment may similarly be applied to any other embodiment disclosed herein.

Figure 1:
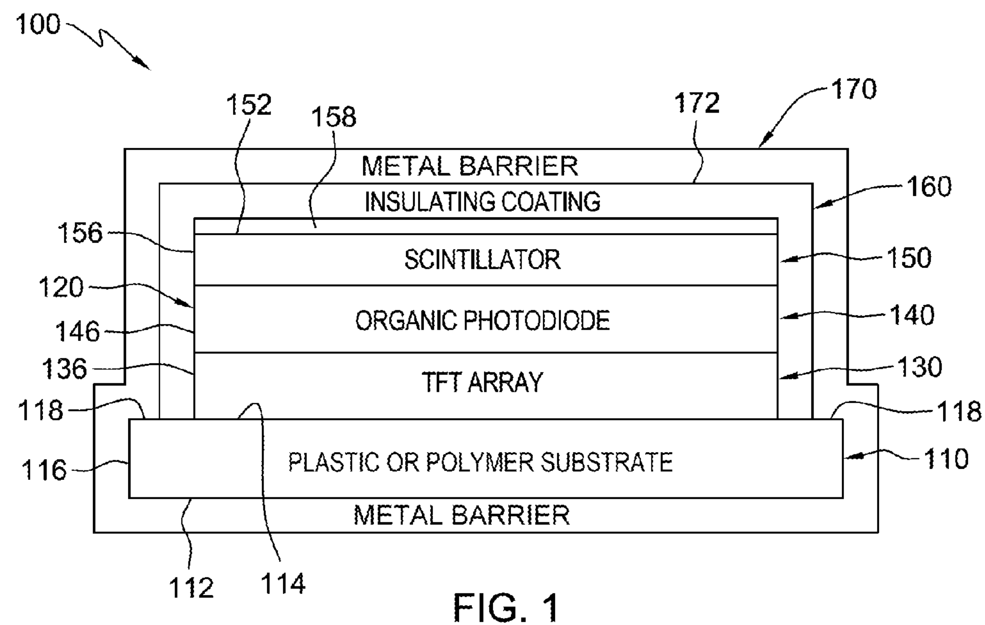
FIG. 1 is a cross-sectional view of one embodiment of an X-ray detector assembly in accordance with aspects of the present disclosure.

FIG. 1 illustrates one embodiment of an X-ray detector assembly 100 in accordance with aspects of the present disclosure. In this illustrated embodiment, X-ray detector assembly 100 may employ a metal material or barrier 170 substantially surrounding an X-ray detector 120. For example, X-ray detector assembly 100 may include a plastic or polymeric substrate 110, X-ray detector 120 having, for example, a TFT (thin-film-transistor) array 130 disposed on the polymeric substrate 110, an organic photodiode 140 disposed on the TFT array 130, a scintillator 150 disposed on the organic photodiode 140, and a metal material or barrier 170 such as a metal coating disposed around X-ray detector 120 supported on polymeric substrate 110.

Polymeric substrate 110 may include a lower surface 112, an upper surface 114, and a peripherally-extending edge 116. TFT array 130 may be disposed on the upper surface 114 of the polymeric substrate 110. TFT array 130 may include a peripherally-extending edge 136, organic photodiode 140 may include a peripherally-extending edge 146, and scintillator 150 may include a peripherally-extending edge 156.

Metal barrier 170 may extend substantially over an upper surface 152 and peripherally-extending edge 156 of scintillator 150, peripherally-extending edge 146 of organic photodiode 140, peripherally-extending edge 136 of TFT array 130, and lower surface 112. For example, the metal barrier 170 may be a continuous one-piece or monolithic metal barrier disposed entirely around the X-ray detector 120 supported on the substrate 110.

An insulating layer 160 may extend between an inner surface 172 of metal barrier 170 and X-ray detector 120. In this illustrated embodiment, insulating layer 160 may be sandwiched between inner surface 172 of metal barrier 170 and upper surface 152 and peripherally-extending edge 156 of scintillator 150, peripherally-extending edge 146 of organic photodiode 140, and peripherally-extending edge 136 of TFT array 130. The insulating layer 160 may electrically insulate metal barrier 170 from the components of the X-ray detector 120. A reflective layer 158 may be disposed between scintillator 150 and insulating layer 160. The lower surface of the reflective layer 158 aids in reflecting light downwardly towards the organic photodiode 140 for increasing the absorption of light by the organic photodiode 140.

It will be appreciated that in X-ray detectors where the peripherally-extending edges of the TFT array 130, organic photodiode 140, and scintillator 150 do not align with each other, the metal barrier 170 and/or insulating layer 160 may extend over peripherally-extending portions of the lower and/or upper surfaces of the TFT array 130, organic photodiode 140, and/or scintillator 150. For example, as shown in FIG. 1, plastic substrate 110 may include a peripherally extending upper edge portion 118 which extends past the peripherally-extending edges 136 of TFT array 130. Metal barrier 170 may extend over a peripherally-extending upper edge portion 118 of polymer substrate 110.

As described above, metal barrier 170 may provide a seal substantially extending around X-ray detector 120 and polymeric substrate 110. In this illustrated embodiment, metal barrier 170 may completely and continuously extend around X-ray detector 120 and polymeric substrate 110. Metal barrier 170 may provide a generally hermetic or airtight seal or closure around X-ray detector 120 and polymeric substrate 110 that acts as a barrier to prevent the exposure of the X-ray detector 120 and polymeric substrate 110 to moisture, oxygen, and/or other gases. Metal barrier 170 may also act as a barrier to chemical attack of the X-ray detector 120 and polymeric substrate 110. Suitable methods for applying the metal barrier 170 or coating may include, but not limited to, physical vapor deposition (PVD), thermal evaporation, sputtering, eBeam, etc.

Figure 2:
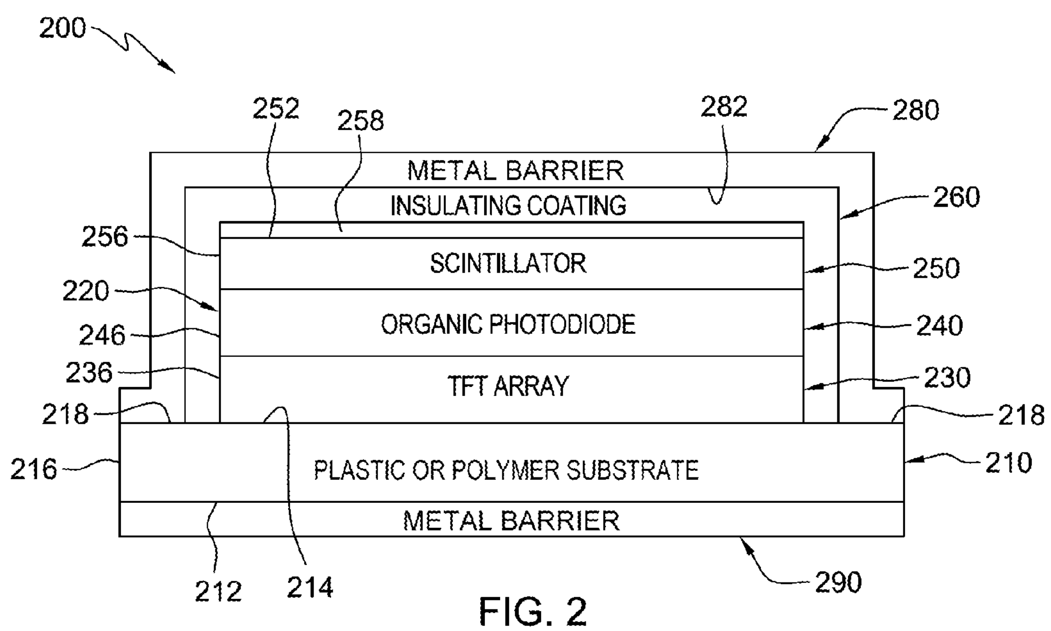
FIG. 2 is a cross-sectional view of another embodiment of an X-ray detector assembly in accordance with aspects of the present disclosure.

FIG. 2 illustrates another embodiment of an X-ray detector assembly 200 in accordance with aspects of the present disclosure. In this illustrated embodiment, X-ray detector assembly 200 may employ a metal barrier 280 and 290 substantially surrounding an X-ray detector. For example, X-ray detector assembly 200 may include a plastic or polymeric substrate 210, an X-ray detector 220 having, for example, a TFT (thin-film-transistor) array 230 disposed on the polymeric substrate 210, an organic photodiode 240 disposed on the TFT array 230, a scintillator 250 disposed on the organic photodiode 240, and metal material or barriers 280 and 290 such as a metal coating disposed around X-ray detector 220 supported on polymeric substrate 210. As described below, metal barrier 280 may be disposed over the X-ray detector 220, and metal barrier 290 may be disposed over the polymeric substrate 210.

Polymeric substrate 210 may include a lower surface 212, an upper surface 214, and a peripherally-extending edge 216. TFT array 230 may be disposed on the upper surface 214 of the polymeric substrate 210. TFT array 230 may include a peripherally-extending edge 236, organic photodiode 240 may include a peripherally-extending edge 246, and scintillator 250 may include a peripherally-extending edge 256.

Metal barrier 280 may extend substantially over an upper surface 252 and peripherally-extending edge 256 of scintillator 250, peripherally-extending edge 246 of organic photodiode 240, and peripherally-extending edge 236 of TFT array 230. Metal barrier 290 may extend substantially over a lower surface 212 of polymeric substrate 210.

An insulating layer 260 may extend between an inner surface 282 of metal barrier 280 and X-ray detector 220. In this illustrated embodiment, insulating layer 260 may be sandwiched between inner surface 282 of metal barrier 280 and upper surface 252 and peripherally-extending edge 256 of scintillator 250, peripherally-extending edge 246 of organic photodiode 240, and peripherally-extending edge 236 of TFT array 230. The insulating layer 260 may electrically insulate metal barrier 280 from the components of the X-ray detector 220. A reflective layer 258 may be disposed between scintillator 250 and insulating layer 260. The lower surface of the reflective layer 258 aids in reflecting light downwardly towards the organic photodiode 240 for increasing the absorption of light by the organic photodiode 240.

It will be appreciated that in X-ray detectors where the peripherally-extending edges of the TFT array 230, organic photodiode 240, and scintillator 250 do not align with each other, the metal barrier 280 and 290 and/or insulating layer 260 may extend over peripherally-extending portions of the lower and/or upper surfaces of the TFT array 230, organic photodiode 240, and/or scintillator 250. As shown in FIG. 2, polymeric substrate 210 may include a peripherally extending portion which extends past the peripherally-extending edges of TFT array 230. Metal barrier 280 may extend over a peripherally-extending upper edge portion 218 of polymer substrate 210. For example, in this illustrated embodiment, peripherally-extending edge portions of the polymer substrate 210 may be sandwiched between the peripheral-extending edge portions of metal barriers 280 and 290.

Metal barriers 280 and 290 may provide a seal substantially extending around X-ray detector 220 and polymeric substrate 210. In this illustrated embodiment, metal barrier 280 may completely and continuously extend over upper surfaces and side surfaces of X-ray detector 220. Metal barrier 290 may extend substantially over the lower surface 212 of polymeric substrate 210. Metal barriers 280 and 290 may provide a generally hermetic or airtight seal or closure around X-ray detector 220 and upper surface 214 and lower surface 212 of polymeric substrate 210 that acts as a barrier to prevent the exposure of the X-ray detector 220 and polymeric substrate 210 to moisture, oxygen, and/or other gases. Metal barriers 280 and 290 may also act as a barrier to chemical attack of the X-ray detector 220 and polymeric substrate 210. Suitable methods for applying the metal barriers or coatings may include, but not limited to, physical vapor deposition (PVD), thermal evaporation, sputtering, eBeam, etc.

Figure 3:
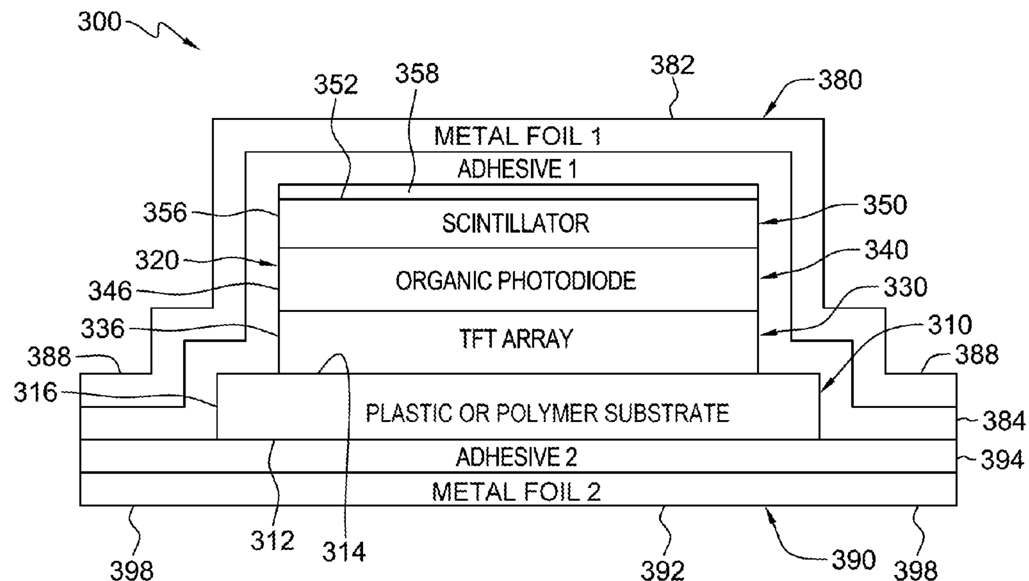
FIG. 3 is a cross-sectional view of another embodiment of an X-ray detector assembly in accordance with aspects of the present disclosure.

FIG. 3 illustrates another embodiment of an X-ray detector assembly 300 in accordance with aspects of the present disclosure. In this illustrated embodiment, X-ray detector system 300 may employ a metal barrier substantially surrounding an X-ray detector 320. For example, X-ray detector assembly 300 may include a plastic or polymeric substrate 310, an X-ray detector 320 having, for example, a TFT (thin-film-transistor) array 330 disposed on the polymeric substrate 310, an organic photodiode 340 disposed on the TFT array 330, a scintillator 350 disposed on the organic photodiode 340, and a metal material or barrier such as adhesively-backed metal foils 380 and 390 disposed substantially around X-ray detector 320 supported on polymeric substrate 310. For example, adhesively-backed metal foils 380 and 390 may include metal foil 382 and 392 having attached to one side of the metal foil adhesive layers 384 and 394, respectively.

In this illustrated embodiment, plastic substrate 310 may include a lower surface 312, an upper surface 314, and a peripherally-extending edge 316. TFT array 330 may be disposed on the upper surface 314 of the plastic substrate 310. TFT array 330 may include a peripherally-extending edge 336, organic photodiode 340 may include a peripherally-extending edge 346, and scintillator 350 may include a peripherally-extending edge 356. The adhesively backed foils may be disposed on and removable from a roll. Alternatively, the adhesively backed foils may be disposed in a sheet form having a releasably attached release sheet (not shown) for protecting the adhesive layer until removal of the release sheet. In still other embodiment, a spray of adhesive may be applied to a surface of the foils. The adhesive layer may act as an insulating layer that extends between the metal foil and the X-ray detector 320 to electrically insulate the metal foil from the components of the X-ray detector 320. A reflective layer 358 may be disposed between scintillator 350 and adhesive layer 384. The lower surface of the reflective layer 358 aids in reflecting light downwardly towards the organic photodiode 340 for increasing the absorption of light by the organic photodiode 340.

In this illustrated embodiment shown in FIG. 3, adhesively-back foil 380 may be draped substantially over and attached to an upper surface 352 of scintillator 350 and draped substantially over or confirm to the peripherally-extending edges of the X-ray detector 320. Adhesively-back foil 390 may be attached substantially over lower surface 312 of polymeric substrate 310. A peripherally-extending portion 388 of adhesively-back foil 380 may extend outwardly from the peripherally-extending side edge of the X-ray detector 320 and the peripherally-extending side edge of the polymeric substrate 310, and a peripherally-extending portion 398 of adhesively-back foil 390 may extend outwardly from the peripherally-extending side edge of the polymeric substrate 310. Peripherally-extending portion 388 of foil 380 may be adhesively attached to peripherally-extending portion 398 of foil 390.

In other embodiments, a single adhesively-backed metal foil may be employed for substantially covering the X-ray detector assembly 300. For example, a single adhesively-backed metal foil may be operably sized so that a first portion may be adhered to the bottom of the polymeric substrate 310 and a second portion folded around one side of the X-ray detector 320, across the top of the scintillator 350, and over the other side of the X-ray detector 320, with a portion of the second portion adhesively attaching to the first portion.

In still other embodiments, an adhesive may be applied to the back of the metal foil or to the outer surfaces of the X-ray detector 320 and lower surface 312 of the polymeric substrate 310 prior to securing the metal foil or foils. In other embodiments, a first foil may be disposed on the lower surface 312 of the polymeric substrate 310, the X-ray detector 320 fabricated on the upper surface 314 of the polymeric substrate 310, and then a second foil disposed over the X-ray detector 320.

Metal foils 380 and 390 may provide a seal substantially extending around X-ray detector 320 and polymeric substrate 310. In this illustrated embodiment, metal foil 380 may completely and continuously extend over an upper surface and side surfaces of X-ray detector 320. Metal foil 390 may extend over the lower surface 312 of polymer substrate 310. Metal foils 380 and 390 may provide a generally hermetic or airtight seal or closure around X-ray detector 320 and upper surface 314 and lower surface 312 of polymeric substrate 310 that acts as a barrier to prevent the exposure of the X-ray detector 320 and polymeric substrate 310 to moisture, oxygen, and/or other gases. Metal foils 380 and 390 may also act as a barrier to chemical attack of the X-ray detector 320 and polymeric substrate 310.

Figure 4:
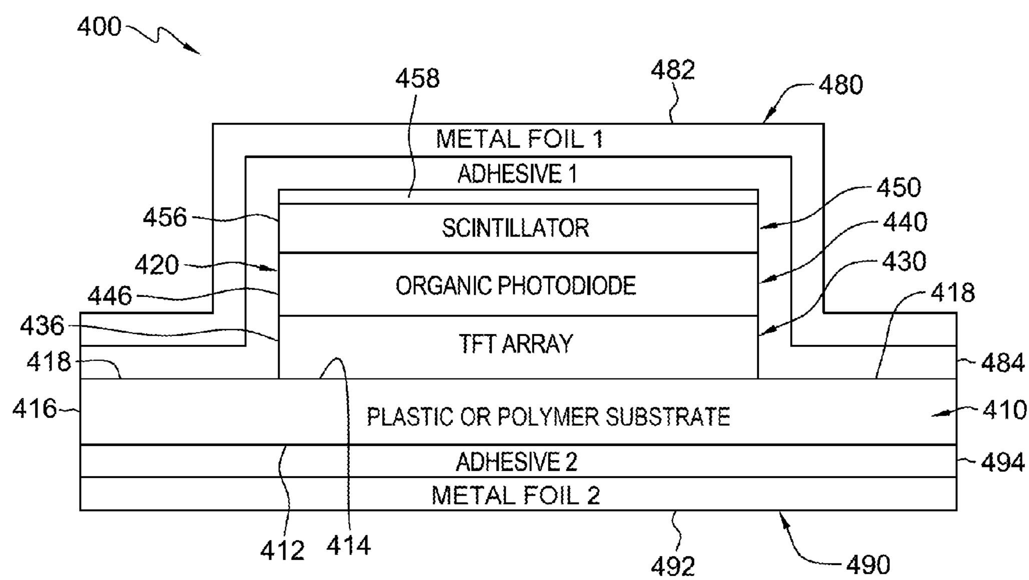
FIG. 4 is a cross-sectional view of another embodiment of an X-ray detector assembly in accordance with aspects of the present disclosure.

FIG. 4 illustrates another embodiment of an X-ray detector assembly 400 in accordance with aspects of the present disclosure. In this illustrated embodiment, X-ray detector assembly 400 may employ a metal foil for substantially surrounding an X-ray detector assembly. For example, X-ray detector assembly 400 may include a plastic or polymeric substrate 410, an X-ray detector 420 having, for example, a TFT (thin-film-transistor) array 430 disposed on the polymeric substrate, an organic photodiode 440 disposed on the TFT array, a scintillator 450 disposed on the organic photodiode, and a metal material or barrier such as an adhesively-backed metal foils 480 and 490 disposed substantially around X-ray detector 420 supported on polymeric substrate 410. For example, the adhesively-backed metal foils 480 and 490 may include metal foil 482 and 492 having attached to one side of the metal foil adhesive layers 484 and 494, respectively.

In this illustrated embodiment, plastic substrate 420 may include a lower surface 412, an upper surface 414, and a peripherally-extending edge 416. TFT array 430 may be disposed on the upper surface of the plastic substrate. TFT array 430 may include a peripherally-extending edge 436, organic photodiode 440 may include a peripherally-extending edge 446, and scintillator 450 may include a peripherally-extending edge 456. The adhesively backed foils may be disposed on and removable from a roll. Alternatively, the adhesively backed foils may be disposed in a sheet form having a releasably attached release sheet (not shown) for protecting the adhesive layer until removal of the release sheet. In still other embodiment, a spray of adhesive may be applied to a surface of the foils. The adhesive layer may act as an insulating layer that extends between the metal foil and the X-ray detector to electrically insulate the metal foil from the components of the X-ray detector. A reflective layer 358 may be disposed between scintillator 350 and adhesive layer 384. The lower surface of the reflective layer aids in reflecting light downwardly towards the photodetector for increasing the absorption of light by the photodetector.

In this illustrated embodiment shown in FIG. 4, adhesively-back foil 480 may be draped substantially over and attached to an upper surface 452 of scintillator 450, draped substantially over or confirm to and attached to the peripherally-extending sides of the X-ray detector 420, and attached to a peripherally-extending upper edge portion 418 of polymer substrate 410. Adhesively-back foil 490 may be disposed substantially over lower surface 412 of substrate 410. For example, in this illustrated embodiment, peripherally-extending edge portions of the polymer substrate may be sandwiched between the peripheral-extending edge portions of metal foils 480 and 490.

In still other embodiments, an adhesive may be applied to the back of the metal foil or to the outer surfaces of the X-ray detector and lower surfaces of the substrate prior to securing the metal foil or foils. In other embodiments, a first foil may be disposed on the bottom surface of the substrate, the X-ray detectors fabricated on top of the substrate, and then a second foil disposed over the X-ray detector.

Metal foils 480 and 490 may provide a seal substantially extending around X-ray detector 420 and polymeric substrate 410. In this illustrated embodiment, metal foils 480 may completely and continuously extend over an upper surface and side surfaces of X-ray detector 420. Metal foils 490 may extend over the lower surface of polymer substrate 410. Metal foils 480 and 490 may provide a generally hermetic or airtight seal or closure around X-ray detector 420 and upper and lower surfaces of polymeric substrate 410 that acts as a barrier to prevent the exposure of the X-ray detector and polymeric substrate to moisture, oxygen, and/or other gases. Metal foils 480 and 490 may also act as a barrier to chemical attack of the X-ray detector and polymeric substrate.

In the various embodiments of the present disclosure, the metal barrier such as the metal coating or metal foil may include a suitable metal material. For example, the metal material may include aluminum, silver, copper, other suitable elemental metals, and/or combinations thereof. The metal barrier may be a solid metal such as a metal barrier composed of substantially entirely a specified metal material or materials, e.g., such as made substantially entirely from aluminum, silver, copper, other metals, and/or combinations thereof. For example, the metal barrier may be an opaque crystalline material, and may exhibit high strength, good electrical and thermal conductivities, ductility, and reflectivity. The metal barrier may be composed of a metal in elemental form, one or more metals or metal alloys, etc. The metal alloy or alloys may comprise metals in elemental form. Suitable materials for the metal barrier substantially does not include metal oxides. For example, a metal barrier may be substantially entirely a metal with, e.g., a thin, light, naturally occurring oxide coating formed on outer surfaces of the barrier metal. A suitable thickness for the metal barrier may range between about 100 nanometers to about 5 millimeters, about 1 micron to about 1 millimeter, or about 1 micron to about 100 microns. The metal barrier may have a constant thickness, or may have a varying thickness around the X-ray detector and substrate.

Suitable adhesive materials include epoxy, acrylate, thermoplastic, thermoset, polyurethane, pressure sensitive coatings and adhesives. Adhesive layer may further include moisture absorbing, oxygen absorbing, and/or additives that improve coating and moisture barrier properties.

Figure 5:
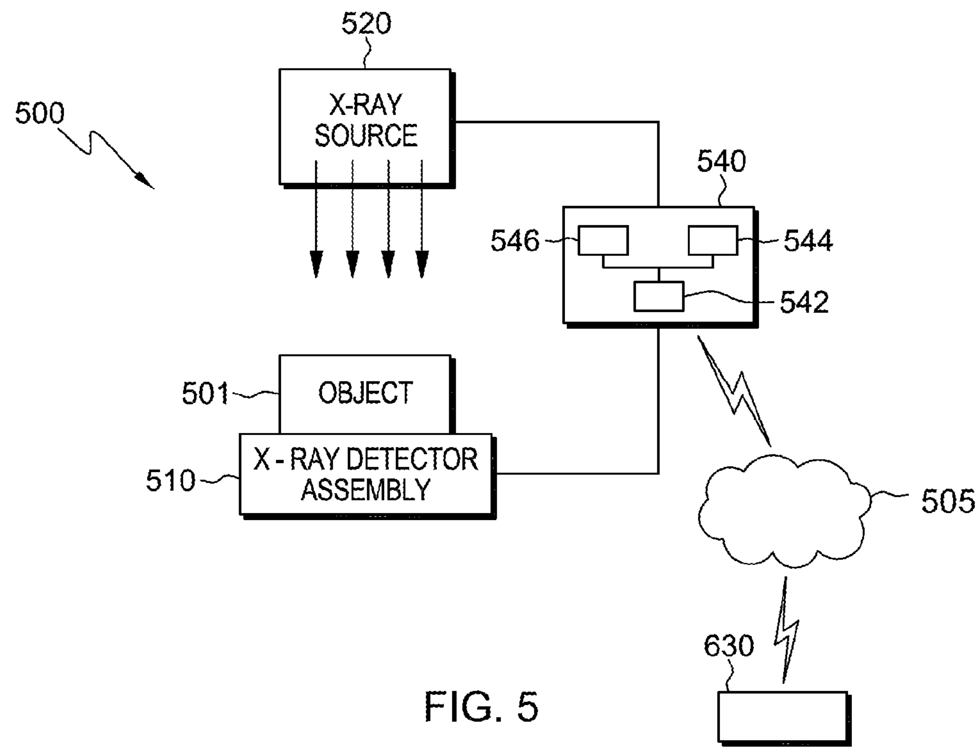
FIG. 5 is a block diagram of one embodiment of an X-ray detector system in accordance with aspects of the present disclosure.

FIG. 5 illustrates a block diagram of an X-ray detector system 500 for imaging an object 501 in accordance with aspects of the present disclosure. For example, X-ray detector system 500 may include an X-ray detector assembly 510, such as the techniques disclosed in X-ray detector assemblies 100 (FIG. 1), 200 (FIG. 2), 300 (FIG. 3), and 400 (FIG. 4), an X-ray source 520, and a computing unit 540. The X-ray source 520 may be, for example, an X-ray tube, and the computing unit 540 may include, for example, a processor or a microcontroller 542, one or more memory devices 544, and one or more input and/or output devices 546. The computing unit 540 may be operable for transmitting to and receiving from a remote computing unit 630 such as via a communications network 505. The communications network 505 may be a global communications network such as the Internet, or a local area network, or other suitable network. Computing unit 540 and/or remote computing unit 630 may be operable for controlling the X-ray source 520 and the X-ray detector assembly 510 for obtaining images, and/or for processing the obtained images. While the illustrated X-ray detector assembly 510 is illustrated as being flat in FIG. 5, it will be appreciated that the X-ray detector assembly 510 may be a non-flat, such as a curved or flexible X-ray detector assembly.

Figure 6:
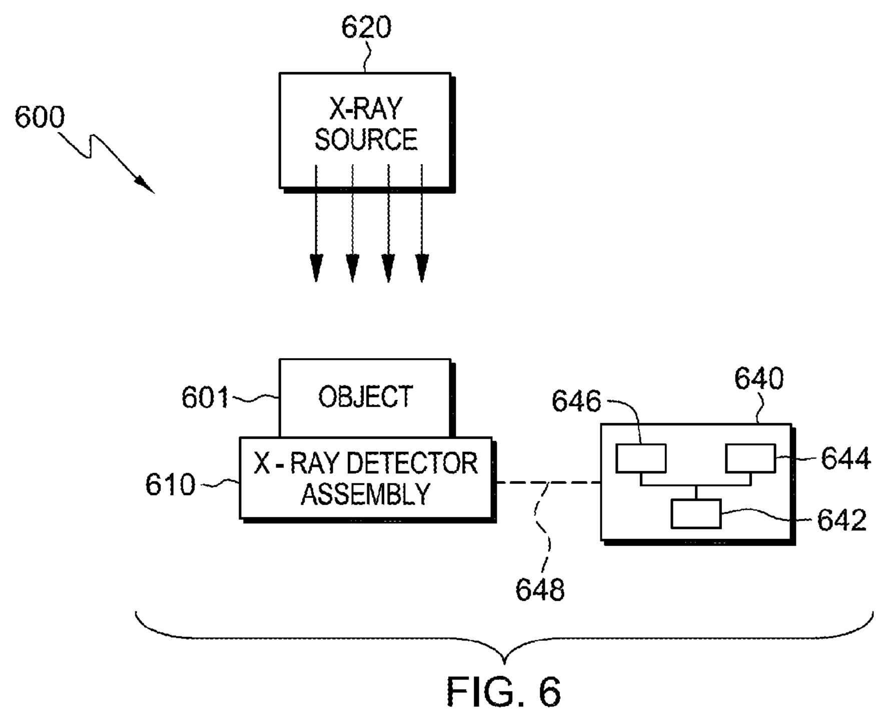
FIG. 6 is a block diagram of another embodiment of an X-ray detector system in accordance with aspects of the present disclosure.

FIG. 6 illustrates a block diagram of an X-ray detector system 600 for imaging an object 601 in accordance with aspects of the present disclosure. For example, X-ray detector system 600 may include an X-ray detector assembly 610, such as the techniques disclosed in X-ray detector assemblies 100 (FIG. 1), 200 (FIG. 2), 300 (FIG. 3), and 400 (FIG. 4), an X-ray source 620, and a computing unit 640. The X-ray source 620 may be, for example, an X-ray tube, and the computing unit 640 may include, for example, a processor or a microcontroller 642, one or more memory devices 644, and one or more input and/or output devices 646. Computing unit 640 may be operably connected to the X-ray detector assembly 610 such as by a wire or a wireless connection 648, e.g., WiFi, for transmitting to and receiving signals and/or data from X-ray detector assembly 610 and/or X-ray source 620. Computing unit 640 may be operable for controlling the X-ray source 620 and the X-ray detector assembly 610 for obtaining images, and/or for processing the obtained images. While the illustrated X-ray detector assembly 610 is illustrated as being flat in FIG. 6, it will be appreciated that the X-ray detector assembly 610 may be non-flat such as a curved or flexible X-ray detector assembly.

Figure 7:
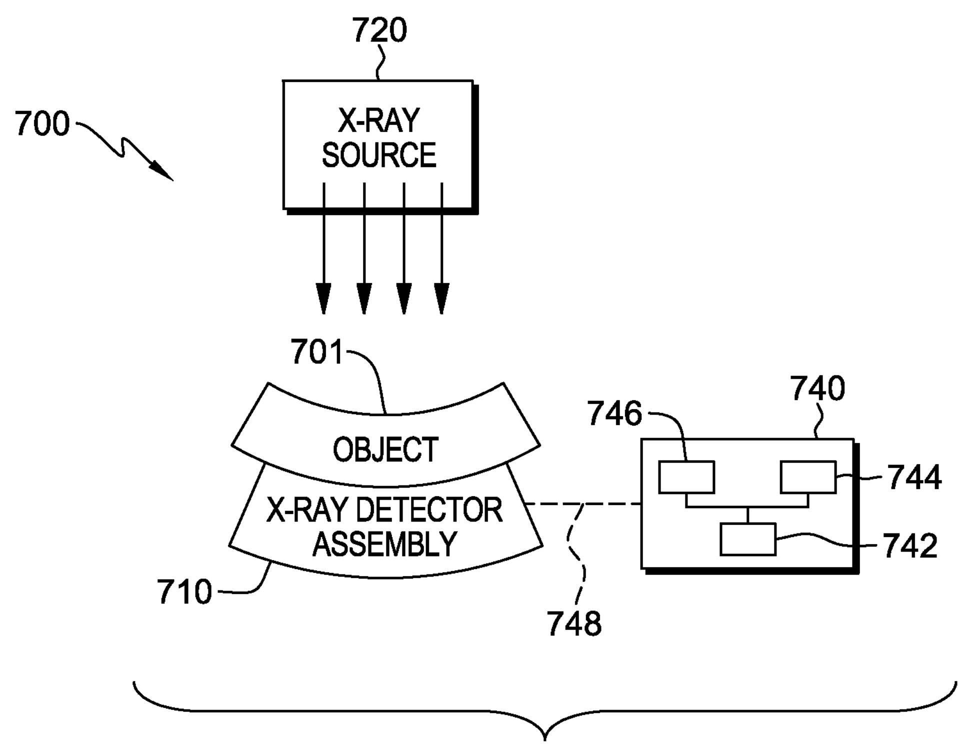
FIG. 7 is a block diagram of another embodiment of an X-ray detector system in accordance with aspects of the present disclosure.

FIG. 7 illustrates a block diagram of an X-ray detector system 700 for imaging an object 701 in accordance with aspects of the present disclosure. For example, X-ray detector system 700 may include an X-ray detector assembly 710, such as X-ray detector assembly employing the techniques disclosed in the X-ray detector assemblies 100 (FIG. 1), 200 (FIG. 2), 300 (FIG. 3), and 400 (FIG. 4), an X-ray source 720, and a computing unit 740. The X-ray source 720 may be, for example, an X-ray tube, and the computing unit 740 may include, for example, a processor or a microcontroller 742, one or more memory devices 744, and one or more input and/or output devices 746. Computing unit 740 may be operably connected to the X-ray detector assembly 710 such as by a wire or a wireless connection 748, e.g., WiFi, for transmitting to and receiving signals and/or data from X-ray detector assembly 710 and/or X-ray source 720. Computing unit 740 may be operable for controlling the X-ray source 720 and the X-ray detector assembly 710 for obtaining images, and/or for processing the obtained images. While the illustrated X-ray detector assembly 710 is illustrated as being curved in FIG. 7, it will be appreciated that the X-ray detector assembly 710 may be a flexible X-ray detector assembly.

In operation, the scintillator converts X-ray photons incident on its surface to optical photons. The optical photons may then be converted to electrical signals by the photodiode. The electrical charges may be stored and read out from storage in the TFT array. These electrical signals are acquired and processed to construct an image of the features (e.g., anatomy, pipe, or other structure) within a target.

Figure 8:
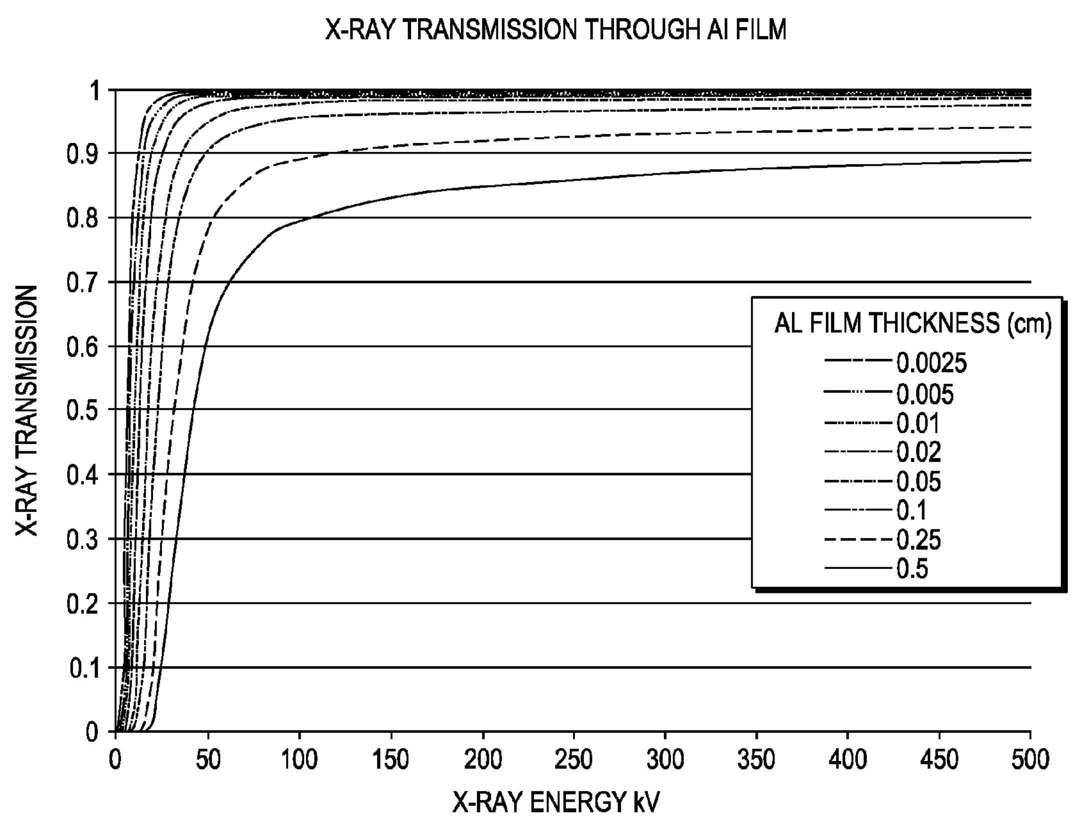
FIG. 8 is a graph of X-ray transmission though various thicknesses of aluminum verses X-ray energy.

The selection of the metal material and the thickness may be adjusted depending on the X-ray source, and the metal material's characteristic absorption coefficient. For instance, as shown in FIG. 8, over 98-percent X-ray transmission may be achieved with about 0.02 centimeter or less of an aluminum coating for about a 70 kV X-ray source, typically used in medical applications, or about 0.1 centimeter or less of an aluminum coating for about a 400 kV X-ray source, typically used for industrial inspection applications.

In the above illustrated embodiments, the polymeric substrate may be composed of a rigid or flexible material. Examples of suitable materials for a polymeric substrate may include rigid or flexible, plastics such as polyethylene terephthalate, polybutylene phthalate, polyethylene naphthalate, polystyrene, polycarbonate, polyether sulfone, polyallylate, polyimide, polycycloolefin, norbornene resins, and fluoropolymers. Other suitable material for a substrate may include glass, which may be metals or metal foils such as stainless steel, aluminum, silver and gold, metal oxides, such as titanium oxide and zinc oxide, and semiconductors such as silicon. Combinations of materials may also be used. By using an unbreakable material instead of a fragile glass substrate for the X-ray detector, the components and materials designed to absorb bending stress or drop shock can be reduced in size and weight or eliminated, and the overall weight and thickness of the detector can be reduced. Removing costly materials which are used to protect the glass substrate decreases the overall cost of the detector. The substrate may have a flat form, curved form, and/or a flexible form. The substrate materials may further include additional functional layers such as a hard-coat, a chemical resistant coating, a planarization/smoothing layer, and other materials, and combinations thereof.

The TFT array may be a two dimensional array of passive or active pixels which store charge for read out by electronics, disposed on an active layer formed of amorphous silicon or an amorphous metal oxide, or organic semiconductors. Suitable amorphous metal oxides include zinc oxide (ZnO), zinc tin oxide, indium oxides, indium zinc oxides (In—Zn—O series), indium gallium oxides, gallium zinc oxides, indium silicon zinc oxides, and indium gallium zinc oxides (IGZO). IGZO materials include $InGaO_3(ZnO)_m$ where m is <6) and $InGaZnO_4$. Suitable organic semiconductors include, but are not limited to, conjugated aromatic materials, such as rubrene, tetracene, pentacene, perylenediimides, tetracyanoquinodimethane and polymeric materials such as polythiophenes, polybenzodithiophenes, polyfluorene, polydiacetylene, poly(2,5-thiophenylene vinylene) and poly(p-phenylene vinylene) and derivatives thereof. Each pixel contains a patterned second electrode 3.

The organic photodiode may include, but not limited to, an organic polymeric semiconductors or an organic compound semiconductors. The photodetector may be fabricated directly over the imaging TFT array. The photodetector 35 may include an anode, a cathode, and an organic film between the anode and cathode which produces charged carriers in response to absorption of light.

The scintillator may be composed of a phosphor material that is capable of converting X-rays to visible light. The wavelength region of light emitted by the scintillator may range from about 360 nm to about 830 nm. Suitable materials for the scintillator include, but are not limited to, organic scintillators, cesium iodide (CsI), CsI (TI) (cesium iodide to which thallium has been added) and terbium-activated gadolinium oxysulfide (GOS), LuOx, BGO, etc. Such materials are commercially available in the form of a sheet or screen. Other suitable forms of the scintillator include a direct-deposited scintillator coating or may be deposited via a particle-in-binder. Prior to applying and sealing the metal barrier, an inert gas such as nitrogen (N2) or argon (Ar) may be introduced to remove ambient air from the X-ray detector.

Figure 9:
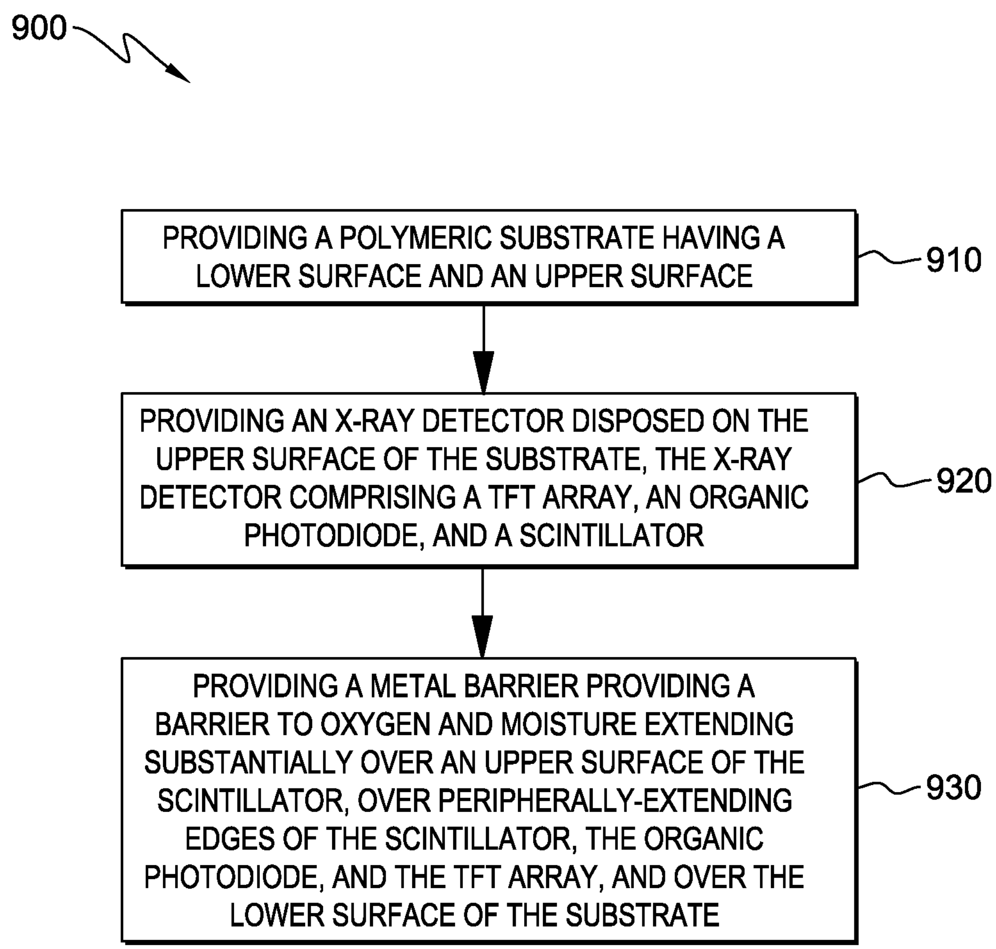
FIG. 9 is a flowchart of one embodiment of a method for forming an organic X-ray detector in accordance with aspects of the present disclosure.

FIG. 9 illustrates one embodiment of a method 900 for fabricating an X-ray detector assembly. In this exemplary embodiment, method 900 may include at 910, providing a polymeric substrate having a lower surface and an upper surface, and at 920, providing an X-ray detector disposed on the upper surface of the polymeric substrate. The X-ray detector includes a TFT (thin-film-transistor) array, an organic photodiode, and a scintillator. At 930, a metal barrier is provided providing a barrier to oxygen and moisture extending substantially over an upper surface of the scintillator, substantially over peripherally-extending edges of the scintillator, the organic photodiode, and the TFT array, and over the lower surface of the polymeric substrate.

It is to be understood that the above description is intended to be illustrative, and not restrictive. Numerous changes and modifications may be made herein by one of ordinary skill in the art without departing from the general spirit and scope of the disclosure as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably" in conjunction with terms such as coupled, connected, joined, sealed or the like is used herein to refer to both connections resulting from separate, distinct components being directly or indirectly coupled and components being integrally formed (i.e., one-piece, integral or monolithic). Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the disclosure has been described in detail in connection with only a limited number of embodiments, it should be readily understood that the disclosure is not limited to such disclosed embodiments. Rather, the disclosure can be modified to incorporate any number of variations, alterations, substitutions or equivalent arrangements not heretofore described, but which are commensurate with the spirit and scope of the disclosure. Additionally, while various embodiments have been described, it is to be understood that aspects of the disclosure may include only some of the described embodiments. Accordingly, the disclosure is not to be seen as limited by the foregoing description, but is only limited by the scope of the appended claims.

This written description uses examples, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. An X-ray detector assembly comprising:

a polymeric substrate having a lower surface and an upper surface;

an X-ray detector disposed on said upper surface of said polymeric substrate, said X-ray detector comprising:

a thin-film-transistor array disposed on said polymeric substrate;

an organic photodiode disposed on said thin-film-transistor array; and a scintillator disposed on said organic photodiode;

a metal barrier extending substantially over an upper surface of said scintillator, substantially over peripherally-extending edges of said scintillator, said organic photodiode, and said thin-film-transistor array, and substantially over said lower surface of said polymeric substrate; and wherein said metal barrier comprises a metal foil and an adhesive layer.

2. The X-ray detector assembly of claim 1, wherein said metal barrier extends continuously over the entire upper surface of said scintillator, and the entire peripherally-extending edges of said scintillator, said organic photodiode, and said thin-film-transistor array.

3. The X-ray detector assembly of claim 1, wherein said metal barrier comprises a continuous monolithic metal barrier extending around the entire X-ray detector supported on said polymeric substrate.

4. The X-ray detector assembly of claim 1, wherein said metal barrier comprises a thickness of at least about 1 micrometer to about 1 millimeter.

5. The X-ray detector assembly of claim 1, further comprising an insulating coating disposed between said metal barrier and a top surface of said scintillator, and disposed between said metal barrier and side edges of said scintillator, said organic photodiode, and said thin-film-transistor array.

6. The X-ray detector assembly of claim 1, wherein said metal barrier extends over said upper surface of said scintillator, over edges of said scintillator, said organic photodiode, and said thin-film-transistor array, and over a lower surface of said polymeric substrate.

7. The X-ray detector assembly of claim 1, wherein said metal barrier comprises an adhesively-backed metal foil.

8. The X-ray detector assembly of claim 1, wherein said metal foil comprises a first metal foil and a first adhesive layer, and a second metal foil and a second adhesive layer.

9. The X-ray detector assembly of claim 8, wherein said first metal foil layer extends over said scintillator, said second metal foil layer extends over a lower surface of said polymeric substrate, and peripherally-extending portions of said first metal foil and said second metal foil are attached together.

10. The X-ray detector assembly of claim 8, wherein said first metal foil extends over said scintillator and operably adhered to an upper surface of said polymeric substrate, and said second metal foil extends over a lower surface of said polymeric substrate.

11. The X-ray detector assembly of claim 1, wherein said metal foil comprises a generally constant thickness.

12. The X-ray detector assembly of claim 1, wherein said metal foil comprises aluminum, silver, copper, and/or combinations thereof.

13. The X-ray detector assembly of claim 1, wherein said X-ray detector is flexible.

14. An X-ray system comprising:

said X-ray detector assembly of claim 1;

an x-ray source; and a controller operable for controlling said X-ray source and said X-ray detector assembly.

15. A method for fabricating an X-ray detector assembly, the method comprising:

providing a polymeric substrate having a lower surface and an upper surface;

providing an X-ray detector disposed on said upper surface of said polymeric substrate, said X-ray detector comprising a thin-film-transistor array, an organic photodiode, and a scintillator;

providing a metal barrier to oxygen and moisture extending substantially over an upper surface of said scintillator, substantially over peripherally-extending edges of said scintillator, said organic photodiode, and said thin-film-transistor array, and substantially over said lower surface of said polymeric substrate; and wherein the providing the metal barrier comprises providing a metal foil and an adhesive layer.

16. The method of claim 15, wherein the providing the metal barrier comprises providing the metal barrier extending continuously over the entire upper surface of the scintillator, and continuously over the entire peripherally-extending edges of said scintillator, said organic photodiode, and said thin-film-transistor array.

17. The method of claim 15, wherein the providing the metal barrier comprises providing a continuous monolithic metal barrier extending around the entire X-ray detector supported on said polymeric substrate.

18. The method of claim 15, further comprising providing, prior to providing the metal barrier, an insulating coating on a top surface of the scintillator, and on side edges of the scintillator, organic photodiode, and thin-film-transistor array.

19. The method of claim 15, wherein the metal foil and the adhesive layer comprise a first metal foil and a first adhesive layer around a portion of the X-ray detector, and a second metal foil and a second adhesive layer around a second portion of the X-ray detector.

20. The method of claim 15, wherein the metal barrier comprises aluminum, silver, copper, or combination thereof.

21. The method of claim 15, wherein the organic photodiode comprises a polymeric organic semiconductor or an organic compound semiconductor.

22. An X-ray detector assembly comprising:

a polymeric substrate having a lower surface and an upper surface;

an X-ray detector disposed on said upper surface of said polymeric substrate, said X-ray detector comprising:

a thin-film-transistor array disposed on said polymeric substrate;

an organic photodiode disposed on said thin-film-transistor array; and a scintillator disposed on said organic photodiode;

a metal barrier extending substantially over an upper surface of said scintillator, substantially over peripherally-extending edges of said scintillator, said organic photodiode, and said thin-film-transistor array, and substantially over said lower surface of said polymeric substrate; and an insulating coating disposed between said metal barrier and a top surface of said scintillator, and disposed between said metal barrier and side edges of said scintillator, said organic photodiode, and said thin-film-transistor array.

23. The X-ray detector assembly of claim 22, wherein said metal barrier extends continuously over the entire upper surface of said scintillator, and the entire peripherally-extending edges of said scintillator, said organic photodiode, and said thin-film-transistor array.

24. The X-ray detector assembly of claim 22, wherein said metal barrier comprises a continuous monolithic metal barrier extending around the entire X-ray detector supported on said polymeric substrate.

25. The X-ray detector assembly of claim 22, wherein said metal barrier comprises a metal foil.

26. An X-ray system comprising:

said X-ray detector assembly of claim 22;

an X-ray source; and a controller operable for controlling said X-ray source and said X-ray detector assembly.

27. A method for fabricating an X-ray detector assembly, the method comprising:

providing a polymeric substrate having a lower surface and an upper surface;

providing an X-ray detector disposed on said upper surface of said polymeric substrate, said X-ray detector comprising a thin-film-transistor array, an organic photodiode, and a scintillator;

providing a metal barrier providing a barrier to oxygen and moisture extending substantially over an upper surface of said scintillator, substantially over peripherally-extending edges of said scintillator, said organic photodiode, and said thin-film-transistor array, and substantially over said lower surface of said polymeric substrate; and providing, prior to providing the metal barrier, an insulating coating on a top surface of the scintillator, and on side edges of the scintillator, said organic photodiode, and said thin-film-transistor array.

28. The method of claim 27, wherein the providing the metal barrier comprises providing the metal barrier extending continuously over the entire upper surface of the scintillator, and continuously over the entire peripherally-extending edges of said scintillator, said organic photodiode, and said thin-film-transistor array.

29. The method of claim 28, wherein in the providing the metal barrier comprises providing a metal coating by physical vapor deposition, thermal evaporation, sputtering, or eBeam.

30. The method of claim 28, wherein in the providing the metal barrier comprises providing a metal foil.

31. The method of claim 27, wherein the providing the metal barrier comprises providing a continuous monolithic metal barrier extending around the entire X-ray detector supported on said polymeric substrate.

32. An X-ray detector assembly comprising:

a polymeric substrate having a lower surface and an upper surface;

an X-ray detector disposed on said upper surface of said polymeric substrate, said X-ray detector comprising:

a thin-film-transistor array disposed on said polymeric substrate;

an organic photodiode disposed on said thin-film-transistor array; and a scintillator disposed on said organic photodiode;

a metal barrier extending substantially over an upper surface of said scintillator, substantially over peripherally-extending edges of said scintillator, said organic photodiode, and said thin-film-transistor array, and substantially over said lower surface of said polymeric substrate; and wherein said X-ray detector is flexible.

33. An X-ray system comprising:

said X-ray detector assembly of claim 32;

an X-ray source; and a controller operable for controlling said X-ray source and said X-ray detector assembly.

34. A method for fabricating an X-ray detector assembly, the method comprising:

providing a polymeric substrate having a lower surface and an upper surface;

providing an X-ray detector disposed on said upper surface of said polymeric substrate, said X-ray detector comprising a thin-film-transistor array, an organic photodiode, and a scintillator;

providing a metal barrier providing a barrier to oxygen and moisture extending substantially over an upper surface of said scintillator, substantially over peripherally-extending edges of said scintillator, said organic photodiode, and said thin-film-transistor array, and substantially over said lower surface of said polymeric substrate; and wherein the X-ray detector is flexible.

* * * * *